(12) United States Patent
Turecek et al.

(10) Patent No.: US 8,637,007 B2
(45) Date of Patent: Jan. 28, 2014

(54) FACTOR VIIA-POLYSIALIC ACID CONJUGATE HAVING PROLONGED IN VIVO HALF-LIFE

(75) Inventors: Peter Turecek, Klosterneuburg (AT); Juergen Siekmann, Vienna (AT); Friedrich Scheiflinger, Vienna (AT); Michel Canavaggio, Vienna (AT); Marie-Christine Canavaggio, legal representative, Vienna (AT)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 714 days.

(21) Appl. No.: 11/956,634

(22) Filed: Dec. 14, 2007

(65) Prior Publication Data

US 2008/0221032 A1  Sep. 11, 2008

Related U.S. Application Data

(60) Provisional application No. 60/875,217, filed on Dec. 15, 2006.

(51) Int. Cl.
*A61K 38/16* (2006.01)
*A61P 7/02* (2006.01)
*C12N 9/96* (2006.01)
*C07K 14/00* (2006.01)

(52) U.S. Cl.
USPC ...... 424/94.3; 424/450; 424/78.17; 514/20.1; 514/23; 530/350

(58) Field of Classification Search
None
See application file for complete search history.

(56) References Cited

U.S. PATENT DOCUMENTS

| | | | |
|---|---|---|---|
| 3,847,890 A | 11/1974 | Green | |
| 4,179,337 A | 12/1979 | Davis et al. | |
| 4,356,170 A | 10/1982 | Jennings et al. | |
| 4,757,006 A | 7/1988 | Toole, Jr. et al. | |
| 4,784,950 A | 11/1988 | Hagen et al. | |
| 4,966,999 A | 10/1990 | Coughlin et al. | |
| 4,970,300 A | 11/1990 | Fulton et al. | |
| 5,122,614 A | 6/1992 | Zalipsky | |
| 5,153,265 A | 10/1992 | Shadle et al. | |
| 5,198,349 A | 3/1993 | Kaufman | |
| 5,198,493 A | 3/1993 | Holmberg et al. | |
| 5,250,421 A | 10/1993 | Kaufman et al. | |
| 5,298,643 A | 3/1994 | Greenwald | |
| 5,492,821 A | 2/1996 | Callstrom et al. | |
| 5,621,039 A | 4/1997 | Hallahan et al. | |
| 5,733,873 A | 3/1998 | Osterberg et al. | |
| 5,846,951 A | 12/1998 | Gregoriadis | |
| 5,874,408 A | 2/1999 | Nayar | |
| 5,919,766 A | 7/1999 | Osterberg et al. | |
| 5,969,040 A | 10/1999 | Hallahan et al. | |
| 6,037,452 A | 3/2000 | Minamino et al. | |
| 6,048,720 A | 4/2000 | Dalborg et al. | |
| 6,183,738 B1 | 2/2001 | Clark | |
| 6,586,398 B1 | 7/2003 | Kinstler et al. | |
| 6,593,294 B1 | 7/2003 | Baru et al. | |
| 6,692,931 B1 | 2/2004 | Reutter et al. | |
| 6,743,908 B2 | 6/2004 | Filpula et al. | |
| 6,806,063 B2 | 10/2004 | Pedersen et al. | |
| 6,872,393 B2 | 3/2005 | Whitlow et al. | |
| 6,913,915 B2 | 7/2005 | Ensor et al. | |
| 7,118,737 B2 | 10/2006 | Kochendoerfer et al. | |
| 7,199,223 B2 | 4/2007 | Bossard et al. | |
| 7,230,081 B1 | 6/2007 | Jensen et al. | |
| 7,338,788 B2 | 3/2008 | Pedersen et al. | |
| 7,645,860 B2 | 1/2010 | Turecek et al. | |
| 7,982,010 B2 | 7/2011 | Turecek et al. | |
| 7,985,838 B2 | 7/2011 | Turecek et al. | |
| 7,985,839 B2 | 7/2011 | Turecek et al. | |
| 8,003,760 B2 | 8/2011 | Turecek et al. | |
| 8,067,543 B2 | 11/2011 | Turecek et al. | |
| 8,071,724 B2 | 12/2011 | Turecek et al. | |
| 8,071,725 B2 | 12/2011 | Turecek et al. | |
| 8,071,726 B2 | 12/2011 | Turecek et al. | |
| 8,071,727 B2 | 12/2011 | Turecek et al. | |
| 8,071,728 B2 | 12/2011 | Turecek et al. | |
| 2002/0110535 A1 | 8/2002 | Jones | |

(Continued)

FOREIGN PATENT DOCUMENTS

| | | |
|---|---|---|
| CA | 2647314 A1 | 11/2007 |
| EP | 0306968 | 3/1989 |

(Continued)

OTHER PUBLICATIONS

Jurlander, B., et al. 2001 Seminars in Thrombosis and Hemostasis 27(4): 373-383.*

(Continued)

*Primary Examiner* — Lisa J Hobbs
(74) *Attorney, Agent, or Firm* — Marshall, Gerstein & Borun LLP

(57) ABSTRACT

The present invention relates to a proteinaceous construct comprising plasmatic or recombinant factor VIIa (FVIIa) or biologically active derivatives thereof, which are bound to a carbohydrate moiety comprising 1-4 sialic acid units, wherein the in vivo half-life of the proteinaceous construct is substantially prolonged in the blood of a mammal, as compared to the in vivo half-life of a FVIIa molecule not bound to a carbohydrate moiety. The invention also provides a method for controlling bleeding in a mammal having a bleeding disorder due to functional defects or deficiencies of FVIIa, FVIII, or FIX. The invention also provides a method for controlling bleeding in a mammal during surgery or trauma.

10 Claims, 8 Drawing Sheets

(56) References Cited

U.S. PATENT DOCUMENTS

| | | |
|---|---|---|
| 2002/0151471 A1 | 10/2002 | Pingel et al. |
| 2003/0143596 A1 | 7/2003 | Bentley et al. |
| 2004/0063911 A1 | 4/2004 | DeFrees et al. |
| 2004/0137557 A1 | 7/2004 | DeFrees et al. |
| 2004/0235734 A1 | 11/2004 | Bossard et al. |
| 2005/0106658 A1 | 5/2005 | Defrees |
| 2005/0113565 A1 | 5/2005 | Klausen et al. |
| 2006/0019877 A1 | 1/2006 | Conradt et al. |
| 2006/0088906 A1 | 4/2006 | DeFrees et al. |
| 2006/0258851 A1 | 11/2006 | Johansen |
| 2006/0276634 A1 | 12/2006 | Nakamura et al. |
| 2007/0191597 A1 | 8/2007 | Jain et al. |
| 2007/0244301 A1 | 10/2007 | Siekmann et al. |
| 2007/0282096 A1 | 12/2007 | Jain et al. |
| 2008/0146771 A1 | 6/2008 | Kozlowski et al. |
| 2008/0260755 A1 | 10/2008 | Metzner et al. |
| 2009/0076237 A1 | 3/2009 | Turecek et al. |
| 2009/0227504 A1* | 9/2009 | Klausen et al. .......... 514/12 |
| 2010/0015684 A1* | 1/2010 | DeFrees et al. .......... 435/188 |
| 2010/0062973 A1* | 3/2010 | Frank et al. .......... 514/8 |

FOREIGN PATENT DOCUMENTS

| | | |
|---|---|---|
| EP | 0605963 | 7/1994 |
| EP | 1 260 582 | 11/2002 |
| EP | 1258497 | 11/2002 |
| WO | WO-91/09122 | 6/1991 |
| WO | WO-92/16555 | 10/1992 |
| WO | WO-94/05332 | 3/1994 |
| WO | WO-94/15625 | 7/1994 |
| WO | WO-94/15626 | 7/1994 |
| WO | WO-94/28024 A1 | 12/1994 |
| WO | WO-94/29370 A1 | 12/1994 |
| WO | WO-95/01804 A1 | 1/1995 |
| WO | WO-96/40731 | 12/1996 |
| WO | WO-96/41813 A2 | 12/1996 |
| WO | WO-97/11957 A1 | 4/1997 |
| WO | WO-98/32466 | 7/1998 |
| WO | WO-99/28455 A1 | 6/1999 |
| WO | WO-99/32134 A1 | 7/1999 |
| WO | WO-00/12587 A2 | 3/2000 |
| WO | WO-00/23114 | 4/2000 |
| WO | WO-00/48635 | 8/2000 |
| WO | WO-01/58935 | 8/2001 |
| WO | WO-01/82943 A2 | 11/2001 |
| WO | WO-01/83725 A1 | 11/2001 |
| WO | WO-02/02764 A2 | 1/2002 |
| WO | WO-02/22776 A2 | 3/2002 |
| WO | WO-02/29025 A2 | 4/2002 |
| WO | WO-02/077218 A1 | 10/2002 |
| WO | WO-03/031464 A2 | 4/2003 |
| WO | WO-03/045980 A2 | 6/2003 |
| WO | WO-03/046150 A2 | 6/2003 |
| WO | WO-04/000366 | 12/2003 |
| WO | WO-2004/014424 A1 | 2/2004 |
| WO | WO-2004/030617 A2 | 4/2004 |
| WO | WO-2004/060965 A2 | 7/2004 |
| WO | WO-2004/075923 | 9/2004 |
| WO | WO-2004/075923 A2 | 9/2004 |
| WO | WO-2004/089280 | 10/2004 |
| WO | WO-2004/091499 | 10/2004 |
| WO | WO-2004/108070 A2 | 12/2004 |
| WO | WO-2005/014024 A2 | 2/2005 |
| WO | WO-2005/014035 A2 | 2/2005 |
| WO | WO-2005/016973 | 2/2005 |
| WO | WO-2005/055950 A2 | 6/2005 |
| WO | WO-2005/070138 A2 | 8/2005 |
| WO | WO-2006/001616 | 1/2006 |
| WO | WO-2006/013202 A2 | 2/2006 |
| WO | WO-2006/016168 A2 | 2/2006 |
| WO | WO-2006/020372 A2 | 2/2006 |
| WO | WO-2006/053299 A2 | 5/2006 |
| WO | WO-2006/071801 | 7/2006 |
| WO | WO-2006/074279 A1 | 7/2006 |
| WO | WO-2006/127896 A2 | 11/2006 |
| WO | WO-2006/134173 A2 | 12/2006 |
| WO | WO-2007/022784 A2 | 3/2007 |
| WO | WO-2007/076062 A2 | 7/2007 |
| WO | WO-2007/140282 A1 | 12/2007 |
| WO | WO-2008/012540 A1 | 1/2008 |
| WO | WO-2008/025856 | 3/2008 |
| WO | WO-2008/035373 A2 | 3/2008 |
| WO | WO-2008/057683 A2 | 5/2008 |
| WO | WO-2008/074032 | 6/2008 |
| WO | WO-2008/081024 A1 | 7/2008 |
| WO | WO-2008/119815 A1 | 10/2008 |
| WO | WO-2009/000522 A1 | 12/2008 |
| WO | WO-2009/006620 A1 | 1/2009 |
| WO | WO-2009/047500 A1 | 4/2009 |
| WO | WO-2009/089396 A2 | 7/2009 |
| WO | WO-2009/108806 A1 | 9/2009 |
| WO | WO-2009/130602 A2 | 10/2009 |
| WO | WO-2009/141418 A1 | 11/2009 |
| WO | WO-2009/141433 A1 | 11/2009 |
| WO | WO-2009/149303 A1 | 12/2009 |
| WO | WO-2010/010324 A1 | 1/2010 |
| WO | WO-2010/062768 A1 | 6/2010 |
| WO | WO-2010/083536 A1 | 7/2010 |
| WO | WO-2010/100430 A1 | 9/2010 |
| WO | WO-2010/102886 A1 | 9/2010 |
| WO | WO-2010/120365 A2 | 10/2010 |
| WO | WO-2010/131015 A1 | 11/2010 |
| WO | WO-2011/012850 A2 | 2/2011 |
| WO | WO-2011/014890 A1 | 2/2011 |
| WO | WO-2011/017055 A2 | 2/2011 |
| WO | WO-2011/018496 A2 | 2/2011 |
| WO | WO-2011/037896 A2 | 3/2011 |
| WO | WO-2011/064247 A1 | 6/2011 |
| WO | WO-2011/101242 A1 | 8/2011 |
| WO | WO-2011/101267 A1 | 8/2011 |
| WO | WO-2011/135307 A1 | 11/2011 |
| WO | WO-2011/135308 A1 | 11/2011 |
| WO | WO-2012/068134 A2 | 5/2012 |
| WO | WO-2013/009627 A2 | 1/2013 |

OTHER PUBLICATIONS

Acharya et al., "Rare bleeding disorder registry: deficiencies of factor II, V, VII, X, XIII, fibrinogen and dysfibrinogenenemias", *J. Thromb. Haemost.*, 2:248-56 (2004).

Biessen et al., "Ligand size is a major determinant of high-affinity binding of fucose- and galactose-exposing (lipo)proteins by the hepatic fucose receptor", *Biochem. J.*, 299:291-6 (1994).

Bjorkman et al., "Pharmacokinetics of coagulation factors: clinical relevance for patients with haemophilia", *Clin. Pharmacokinet.*, 40:815-32 (2001).

Eigenbrot, "Structure, function, and activation of cogaulation factor VII", *Curr. Protein Peptide Sci.*, 3:287-99 2002.

Fernandes et al., "Polysialylated asparaginase: preparation, activity and pharmacokinetics", *Biochim. Biophys. Acta.*, 1341:26-34 (1997).

Fernandes et al., "The effect of polysialylation on the immunogenicity and antigenicity of asparaginase: implication in its pharmacokinetics", *Int. J. Pharm.*, 217:215-24 (2001).

GenBank accession No. J02933, Human blood coagulation factor VII gene, complete cds, Nov. 1, 1994.

GenBank accession No. M13232, Human factor VII serine protease precursor mRNA, complete cds, clone lambda-HVII2463, Feb. 13, 1996.

GenBank accession No. P08709, RecName: Full=Coagulation factor VII; AltName: Full=Serum prothrombin conversion accelerator; Short=SPCA; AltName: Full=Proconvertin; AltName: INN=Eptacog alfa; Contains: RecName: Full=Factor VII light chain; Contains: RecName: Full=Factor VII heavy chain; Flags: Precursor, Mar. 3, 2009.

Hagen et al., "Characterization of a cDNA coding for human factor VII", *Proc. Natl. Acad. Sci. USA*, 83:2412-6 (1986).

Harris et al., "Effect of pegylation on pharmaceuticals", *Nat. Rev. Drug Discov.*, 2:214-21 2003.

Hedner, "Mechanism of action, development and clinical experience of recombinant FVIIa", *J. Biotechnol.*, 124:747-57 (2006).

(56) References Cited

OTHER PUBLICATIONS

Jennings et al., "Immunochemistry of groups A, B, and C meningococcal polysaccharide-tetanus toxoid conjugates", *J. Immunol.*, 127:1011-8 (1981).
Kang et al., "Asymetric synthesis of N-acetylneuraminic acid", Chem. Commun., 227-8 2000.
Klausen et al., "Analysis of the glycoforms of human recombinant factor VIIa by capillary electrophoresis and high-performance liquid chromatography", *J. Chromatogr. A*, 718:195-202 (1995).
Mariani et al., "Steps towards an effective treatment strategy in congenital factor VII deficiency", *Semin. Hematol.*, 43:S42-7 (2006).
Pinotti et al., "Modulation of factor VII levels by intron 7 polymorphisms: population and in vitro studies", *Blood*, 95:3423-8 (2000).
Ress et al., "Sialic Acid Donors: Chemical Synthesis and Glycosylation", *Curr. Org. Synthesis*, 1:31-46 (2004).
Sabater-Lleal et al., "Human F7 sequence is split into three deep clades that are related to FVII plasma levels", *Hum. Genet.*, 118:741-51 (2006).
Schenone et al., "The blood coagulation cascade", *Curr. Opin. Hematol.*, 11;272-7 (2004).
Abuchowski et al., Cancer therapy with chemically modified enzymes. I. Antitumor properties of polyethylene glycol-asparaginase conjugates. *Cancer Biochem. Biophys.* 7: 175-86 (1984).
Baxter announces collaborations to develop longer acting forms of blood clotting factors. *Baxter News (online)*, Sep. 29, 2005.
Bi et al., Target disruption of the mouse factor VII gene produces a model of Haemophilia A. *Nat. Genet.* 10: 119-21 (1995).
Caliceti et al., Pharmacokinetics of pegylated interferons: What is misleading? *Digest. Liver Dis.* 36(Suppl. 3): S334-9 (2004).
Jain et al., Polysialylation: The natural way to improve the stability and pharmacokinetics of protein and peptide drugs. http://www.lipoxen.co.uk/media/48760/dsd%20and%20s%20pp3-9.pdf, Jul. 2004.
Kozlowski et al., Development of pegylated interferons for the treatment of chronic Hepatitis C. *BioDrugs.* 15(7): 419-29 (2001).
Nektar Advanced PEGylation Catalog 2005-2006, p. 30 (2005).
Nektar Advanced PEGylation Price List 2005-2006, p. 11 (2005).
NOF Corporation DDS Catalogue, p. 58 (2005).
Roberts et a., Chemistry for peptide and protein pegylation *Adv. Drug Del. Rev.* 54: 459-76 (2002).
Rosen et al., Assay of factor VIII: C with a chromogenic substrate. *Scand J. Haematol.* 33(Suppl. 40): 139-45 (1984).
Rostin et al., B-domain deleted recombinant coagulation factor VIII modified with monomethoxy polyethylene glycol. *Bioconjugate Chem.* 11: 387-96 (2000).
Saenko et al., Strategies towards a longer acting factor VIII. *Haemophilia.* 12: 42-51 (2006).
Sakuragawa et al., Studies on the stability of factor VIII modified by polyethylene glycol. *Acta Med. Biol.* 36:1-5 (1988).
Seffernick et al., Melamine deaminase and atrazine chlorohydrolase: 98% identical but functionally different. *J. Bacteriology.* 2405-10 (2001).
Severs et al., Characterization of PEGylated factor VIII molecules. *Blood.* 108: 11-12 (2006). Abstract.
Study shows molecular size and structure of PEG interferon molecules, as used in pegintron(R), affect antiviral activity in vitro. *Hispanic PR Wire*, Oct. 28, 2003.
Thim et al., Amino acid sequence and posttranslational modifications of human factor VIIa from plasma and transfected baby hamster kidney cells. *Biochemistry*, 27:7785-93 (2004).
Tsubery et al., Prolonging the action of protein and peptide drugs by a novel approach of reversible polyethylene glycol modification. *J. Biol. Chem.* 279(37): 38118-24 (2004).
Tsutsumi et al., Site-specific chemical modification with polyethylene glycol of recombinant immunotoxin anti-Tac(Fv)-PE38 (LMB-2) improves antitumor activity and reduces animal toxicity and immunogenicity. *Proc. Natl. Acad. Sci. USA.* 97: 8548-53 (2000).
Urrutigoity et al., Biocatalysis in organic solvents with a polymer-bound horseradish peroxidase. *Biocatalysis.* 2: 145-9 (1989).
Veronese et al., Bioconjugation in pharmaceutical chemistry. *IL Farmaco.* 54: 497-516 (1999).
Weber et al., Characterization of glycopeptides from recombinant coagulation factor VIIa by high-performance liquid chromatography and capillary zone electrophoresis using ultraviolet and pulsed electrochemical detection. *Anal. Biochem.*, 225: 135-42 (1995).
Wells et al., Additivity of mutational effects in proteins. *Biochemistry.* 29(37): 8509-17 (1990).
Wilchek et al., Labeling glycoconjugates with hydrazide reagents. *Methods Enzymol.* 138: 429-42 (1987).
Zalipsky et al., Hydrazide derivatives of poly(ethylene glycol) and their bioconjugates. Poly(ethylene glycol) Chemistry and Biological Applications. Chapter 21, pp. 318-341 (1997).
Cordes et al., Nucleophilic catalysis of semicarbazone formation by anilines. *J. Am. Chem. Soc.*, 84: 826-31 (1962).
Dirksen et al., Nucleophilic catalysis of hydrazone formation and transimination: Implications for dynamic covalent chemistry. *J. Am. Chem. Soc.*, 128: 15602-3 (2006).
Dirksen et al., Nucleophilic catalysis of oxime ligation. *Ange. Chem. Int. Ed.*, 45(45): 7581-4 (2006).
Dirksen et al., Rapid oxime and hydrazone ligations with aromatic aldehyres for biomolecular labeling. *Bioconj. Chem.*, 19(12): 2543-8 (2008).
Gregoriadis et al., Improving the therapeutic efficacy of peptides and proteins: A role for polysialic acids. *Int. J. Pharmaceut.*, 300(1-2): 125-30 (2005).
Jiang et al., Chemistry for pegylation of protein and peptide molecules, *Chin. J. Organ. Chem.*, 23(12): 1340-7 (2003).—English Abstract.
Kohler, Aniline: A catalyst for sialic acid detection. *ChemBioChem*, 10: 2147-50 (2009).
Lees et al., Versatile and efficient synthesis of protein-polysaccharide conjugate vaccines using aminooxy reagents and oxime chemistry. *Vaccine*, 24(6): 716-29 (2006).
Reglero et al., Polysialic acids. *Int. J. Biochem.*, 23(11): 1517-27 (1993).
Thygesen et al., Nucleophilic catalysis of carbohydrate oxime formation by anilines. *J. Org. Chem.*, 75: 1752-5 (2010).
Zeng et al., High-efficency labeling of sialylated glycoproteins on living cells. *Nat. Methods*, 6(3): 207-9 (2009).
Great Britain Search Report and Written Opinion, GB-1012482.4, dated Nov. 24, 2010.
International Search Report and Written Opinion of the International Searching Authority, PCT/US2007/007560, European Patent Office, dated Sep. 18, 2007.
International Preliminary Report on Patentability, PCT/US2007/007560, dated Sep. 30, 2008.
International Search Report and Written Opinion of the International Searching Authority, PCT/US2009/052103, European Patent Office, dated Feb. 12, 2010.
International Preliminary Report on Patentability, PCT/US2009/052103, dated Feb. 1, 2011.
International Search Report and Written Opinion, PCT/US2010/043242, dated Feb. 10, 2011.
International Preliminary Report on Patentability, PCT/US2010/043242, dated Jan. 31, 2012.
International Search Report and Written Opinion of the International Searching Authority, PCT/GB2010/001422, European Patent Office, dated Feb. 4, 2011.
International Preliminary Report on Patentability, PCT/GB2010/001422, dated Jan. 31, 2012.

\* cited by examiner

FACTOR VIIA-POLYSIALIC ACID CONJUGATE HAVING PROLONGED IN VIVO HALF-LIFE

CROSS-REFERENCE TO RELATED APPLICATION

This application claims priority to U.S. Provisional Application No. 60/875,217 filed Dec. 15, 2006.

FIELD OF THE INVENTION

The present invention relates to a proteinaceous construct comprising coagulation factor VIIa (FVIIa) being bound to a carbohydrate moiety comprising a chain of 1-4 sialic acid units. Further the present invention relates to methods for prolonging the in vivo-half-life of blood coagulation proteins, especially FVIIa in the blood of a mammal having a bleeding disorder associated with functional defects or deficiencies of at least FVIIa, factor VIII (FVIII) and factor IX (FIX).

BACKGROUND OF THE INVENTION

The blood coagulation cascade is divided into three distinct segments: the intrinsic, extrinsic, and common pathways (Schenone et al., Curr Opin Hematol. 2004; 11:272-7). The cascade involves a series of serine protease enzymes (zymogens) and protein cofactors. When required, an inactive zymogen precursor is converted into the active for which consequently converts the next enzyme in the cascade.

The intrinsic pathway requires the clotting factors VIII, IX, X, XI, and XII. Initiation of the intrinsic pathway occurs when prekallikrein, high-molecular-weight kininogen, factor XI (FXI) and factor XII (FXII) are exposed to a negatively charged surface. Also required are calcium ions and phospholipids secreted from platelets.

The extrinsic pathway is initiated when the vascular lumen of blood vessels is damaged. The membrane glycoprotein tissue factor is exposed and then binds to circulating factor VII (FVII) and to small preexisting amounts of its activated for FVIIa. This binding facilitates full conversion of FVII to FVIIa and subsequently, in the presence of calcium and phospholipids, the conversion of factor IX (FIX) to factor IXa (FIXa) and factor X (FX) to factor Xa (FXa). The association of FVIIa with tissue factor enhances the proteolytic activity by bringing the binding sites of FVII for the substrate (FX and FIX) into closer proximity and by inducing a conformational change, which enhances the enzymatic activity of FVIIa. The rate of FX activation by the extrinsic pathway is approximately 50 times slower than the rate achieved by the (intrinsic) pathway of FIXa, FVIIIa, phospholipid, and calcium ions.

The activation of FX is the common point of the two pathways. Along with phospholipid and calcium, factors Va (FVa) and Xa convert prothrombin to thrombin (prothrombinase complex), which then cleaves fibrinogen to form fibrin monomers. The monomers polymerize to form fibrin strands. Factor XIIIa (FXIIIa) covalently bonds these strands to one another to form a rigid mesh.

Conversion of FVII to FVIIa is also catalyzed by a number of proteases, including thrombin, FIXa, FXa, factor XIa (FXIa), and factor XIIa (FXIIa). For inhibition of the early phase of the cascade, tissue factor pathway inhibitor targets FVIIa/tissue factor/FXa product complex.

FVII (also known as stable factor or proconvertin) is a vitamin K-dependent serine protease glycoprotein with a pivotal role in hemostasis and coagulation (Eigenbrot, Curr Protein Pept Sci. 2002; 3:287-99).

FVII is synthesized in the liver and secreted as a single-chain glycoprotein of 48 kD. FVIIa shares with all vitamin K-dependent serine protease glycoproteins a similar protein domain structure consisting of an amino-terminal gamma-carboxyglutamic acid (Gla) domain with 9-12 residues responsible for the interaction of the protein with lipid membranes, a carboxy-terminal serine protease domain (catalytic domain), and two epidermal growth factor-like domains containing a calcium ion binding site that mediates interaction with tissue factor.

Gamma-glutamyl carboxylase catalyzes carboxylation of Gla residues in the amino-terminal portion of the molecule. The carboxylase is dependent on a reduced form of vitamin K for its action, which is oxidized to the epoxide form. Vitamin K epoxide reductase is required to convert the epoxide form of vitamin K back to the reduced form.

The major proportion of FVII circulates in plasma in zymogen form, and activation of this form results in cleavage of the peptide bond between arginine 152 and isoleucine 153. The resulting activated FVIIa consists of a NH$_2$-derived light chain (20 kD) and a COOH terminal-derived heavy chain (30 kD) linked via a single disulfide bond (Cys 135 to Cys 262). The light chain contains the membrane-binding Gla domain, while the heavy chain contains the catalytic domain.

The plasma concentration of FVII determined by genetic and environmental factors is about 0.5 mg/mL (Pinotti et al., Blood. 2000; 95:3423-8). Different FVII genotypes can result in several-fold differences in mean FVII levels. Plasma FVII levels are elevated during pregnancy in healthy females and also increase with age and are higher in females and in persons with hypertriglyceridemia. FVII has the shortest half-life of all procoagulant factors (3-6 h). The mean plasma concentration of FVIIa is 3.6 ng/mL in healthy individuals and the circulating half-life of FVIIa is relatively long (2.5 h) compared with other coagulation factors.

Hereditary FVII deficiency is a rare autosomal recessive bleeding disorder with a prevalence estimated to be 1 case per 500,000 persons in the general population (Acharya et al., J Thromb Haemost. 2004; 2248-56). Acquired FVII deficiency from inhibitors is also very rare. Cases have also been reported with the deficiency occurring in association with drugs such as cephalosporins, penicillins, and oral anticoagulants. Furthermore, acquired FVII deficiency has been reported to occur spontaneously or with other conditions, such as myeloma, sepsis, aplastic anemia, with interleukin-2 and antithymocyte globulin therapy.

Replacement therapy is the mainstay of treatment for patients with FVII deficiency (Mariani et al., Semin Hematol. 2006; 43(Suppl 1):S42-7). This has traditionally been achieved using, fresh frozen plasma (FFP), prothrombin complex concentrates (PCCs), or plasma-derived FVII concentrates. However, recombinant FVIIa (rFVIIa) is now widely used for therapy in these patients.

RFVIIa has also been developed for treatment of bleedings in hemophilia A and B patients with inhibitors, and has been found to induce hemostasis even during major surgery such as major orthopedic surgery (Hedner, J. Biotechnol. 2006; 124: 747-57). RFVIIa is being produced in BHK cell cultures and has been shown to be very similar to plasma-derived FVIIa. The use of rFVIIa in hemophilia treatment is based on the low affinity binding of FVIIa to the surface of thrombin activated platelets. By the administration of pharmacological doses of exogenous rFVIIa the thrombin generation on the platelet surface at the site of injury is enhanced independently of the presence of FVIII/FIX. As a result of the increased and rapid thrombin formation, a tight fibrin hemostatic plug is being formed.

Although originally developed for the treatment of FVII deficiency and inhibitor-complicated hemophilia A and B, novel indications for rFVIIa (based on case reports and smaller clinical trials) include use in patients with liver disease, thrombocytopenia, or qualitative platelet dysfunction and in patients with no coagulation disorders who are bleeding as a result of extensive surgery or major trauma.

Therapeutic polypeptide drugs such as blood coagulation protein including FVIIa are rapidly degraded by proteolytic enzymes and neutralized by antibodies. This reduces their half-life and circulation time, thereby limiting their therapeutic effectiveness. Relatively high doses and frequent administration are necessary to reach and sustain the desired therapeutic or prophylactic effect of FVIIa. As a consequence adequate dose regulation is difficult to obtain and the need of frequent intravenous administrations imposes restrictions on the patient's way of living. Thus an improved FVIIa molecule with a longer circulation half-life would decrease the number of necessary administrations.

In principal, there are four general options for half-life extension of proteins in the blood circulation:
  Direct chemical or enzymatic modification
  Use of carrier molecules to protect the proteins in the circulation
  Construction of mutants to extent half-life
  Modification of the degradation pathway.

The present invention teaches an improvement of blood coagulation proteins, especially the FVIIa molecule by chemical modification. For chemical modification of therapeutic polypeptides several approaches have been used in the past.

PEGylation of polypeptide drugs protects them and improves their pharmacodynamic and pharmacokinetic profiles (Harris and Chess, Nat Rev Drug Discov. 2003; 2:214-21) The PEGylation process attaches repeating units of polyethylene glycol (PEG) to a polypeptide drug. PEG molecules have a large hydrodynamic volume (5-10 times the size of globular proteins), are highly water soluble and hydrated, very mobile, non-toxic, non-immunogenic and rapidly cleared from the body. PEGylation of molecules can lead to increased resistance of drugs to enzymatic degradation, increased half-life in vivo, reduced dosing frequency, decreased immunogenicity, increased physical and thermal stability, increased solubility, increased liquid stability, and reduced aggregation. The first PEGylated drugs were approved by the FDA in the early 1990s. In the meantime the FDA approved several PEGylated drugs for oral, injectable, and topical administration.

GlycoPEGylation™ technology includes methods that provide a peptide conjugate between a PEG polymer and a peptide, with the PEG covalently attached to the peptide via an intact glycosyl-linking group.

Liposomes have been used to encapsulate a variety of molecules such as DNA, anti-sense RNA, antibiotics, anti-cancer, and anti-fungal drugs, inhibitors/activators, antibodies (immunoliposomes), and antigens (for vaccines).

Phospholipids can be also conjugated to PEGs (PEG-liposome) for example via an amide linkage, carboxy-PEG and purified soy phosphatidylethanolamine (PE), esters and carbamate derivatives, the carbamate derivative being the most widely used today (U.S. Pat. No. 6,593,294). The molecular weights of the most commonly used PEG's are 2,000 and 5,000, but PEG's ranging from 600 to 12,000 are also used.

Acidic monosaccharide-substituted proteins were first disclosed in U.S. Pat. No. 3,847,890. In this patent acidic monosaccharides, i.e. n-acetylneuraminic acid and gluconate were substituted onto α-amino or ε-amino groups of insulin, human growth hormone or albumin to reduce the antigenicity of the polypeptides.

Polysialic acid (PSA), also referred as colominic acid (CA), is a naturally occurring polysaccharide. It is a homopolymer of N-acetylneuraminic acid with α(2-8) ketosidic linkage and contains vicinal diol groups at its non-reducing end. It is negatively charged and a natural constituent of the human body. It can easily be produced from bacteria in large quantities and with pre-determined physical characteristics (U.S. Pat. No. 5,846,951). Being chemically and immunologically identical to polysialic acid in the human body, bacterial polysialic acid is non-immunogenic, even when coupled to proteins. Unlike other polymers (eg. PEG), polysialic acid is biodegradable. Covalent coupling of colominic acid to catalase and asparaginase led to an increase of enzyme stability in the presence of proteolytic enzymes or blood plasma. Comparative studies in vivo with polysialylated and unmodified asparaginase revealed that polysialylation increased the half-life of the enzyme (Fermandes and Gregoriadis, Int J. Pharm. 2001; 217:215-24)

However, to date no therapeutic compounds consisting of a polypeptide conjugated to an acidic monosaccharide as described in U.S. Pat. No. 3,847,890 are commercially available. In contrast, U.S. Pat. No. 5,846,951 teaches that the polysaccharide portion of the compound should have at least 5, and in other embodiments at least 20 or 50 sialic acid residues in the polymer chain. Because the polysaccharides are usually produced in bacteria carrying the inherent risk of copurifying endotoxins, the purification of long sialic acid polymer chains may raise the probability of increased endotoxin content. Short PSA molecules with a 1-4 sialic acid units can also be synthetically prepared (Kang et al., Chem. Commun. 2000; 227-8; Ress and Linhardt, Current Organic Synthesis. 2004; 131-46), thus minimizing the risk of high endotoxin levels.

WO 98/32466A1 suggests that FVII, among many other proteins, may be PEGylated but does not contain any working examples supporting the disclosure.

WO 01/58935A3 teaches conjugates comprising at least one non-polypeptide moiety covalently attached to a polypeptide, wherein the amino acid sequence of the polypeptide differs from that of wild-type FVII or FVIIa in that at least one amino acid residue comprising an attachment group for said non-polypeptide moiety has been introduced or removed. For the non-polypeptide moieties especially PEG was suggested.

US20050113565A1 discloses a FVII polypeptide or FVII-related polypeptide, wherein the polypeptide comprises one or more asparagine-linked and/or serine-linked oligosaccharide chains, and wherein at least one of said oligosaccharide groups is covalently attached to at least one polymeric group (PEG, "glycoPEGylation").

Thus, there remains a need in the art for compositions and methods that provide clotting protein preparations comprising improved plasma derived or rFVII, modified FVII, or FVII-related polypeptide.

SUMMARY OF THE INVENTION

The present invention provides a proteinaceous construct comprising plasmatic or recombinant factor VIIa (FVIIa) or biologically active derivatives thereof, said FVIIa or said biologically active derivatives thereof being bound to a chain of 1-4 sialic acid units, wherein the in vivo-half-life of the proteinaceous construct is substantially prolonged in the blood of a mammal, particularly a human, compared to FVIIa or derivatives thereof lacking a chain of 1-4 sialic acid units. Additionally, pharmaceutical compositions containing said proteinaceous construct as well as methods for prolonging the in vivo-half-life of FVIIa in the blood of a mammal having a bleeding disorder associated with functional defects or deficiencies of at least one of FVIIa, FVII and FIX using said proteinaceous construct are provided according to the present invention. The proteinaceous construct of the invention can also be administered to control bleeding in ease of trauma or surgery in a mammal with normal levels of coagulation factors.

in one embodiment of the invention, a proteinaceous construct is provided comprising (a) an activated factor VII: (FVIIa) molecule selected from the group consisting of plasmatic FVIIa, recombinant FVIIa (rFVIIa), and a biologically active derivative of FVIIa; and (b) at least one physiologically acceptable carbohydrate moiety comprising 1-4 sialic acid units bound to said FVIIa molecule, wherein the in vivo half-life of said construct is prolonged in the blood of a mammal as compared to the in vivo half-life of a FVIIa molecule that is not bound to said carbohydrate moiety.

In another embodiment of the invention, the aforementioned proteinaceous construct is provided wherein the in vivo half-life of said construct is increased by at least a factor of about two as compared to the in vivo half-life of a FVIIa molecule that is not bound to said carbohydrate moiety. In another embodiment, the aforementioned proteinaceous construct is provided wherein the in vivo half-life of said construct is increased by at least a factor of about three as compared to the in vivo half-life of a FVIIa molecule that is not bound to said carbohydrate moiety. In still another embodiment, the aforementioned proteinaceous construct is provided wherein the physiologically acceptable carbohydrate moiety is directly covalently linked to at least one amino acid residue of said FVIIa molecule.

In yet another embodiment of the invention, the aforementioned proteinaceous construct is provided wherein the physiologically acceptable carbohydrate moiety is non-covalently linked to at least one amino acid residue of said FVIIa molecule. In still another embodiment, the aforementioned proteinaceous construct is provided wherein said physiologically acceptable carbohydrate moiety is a polysialic acid or a derivative thereof.

In one embodiment of the invention, a pharmaceutical composition is provided comprising an effective amount of the aforementioned proteinaceous construct and one or more compounds selected from the group consisting of a pharmaceutically acceptable carrier, diluent, salt, buffer, and excipient.

In another embodiment of the invention, a method of controlling bleeding in a mammal having a bleeding disorder associated with functional defects or deficiencies of at least one of FVIIa, FVIII and FIX is provided comprising administering the aforementioned proteinaceous construct. In yet another embodiment, a method of controlling bleeding in a mammal during surgery or trauma is provided comprising administering the aforementioned proteinaceous construct.

In still another embodiment of the invention, a kit is provided comprising an effective amount of the aforementioned proteinaceous construct, packaged in a container, wherein the kit optionally contains a second therapeutic agent, and further comprising a label attached to or packaged with the container, the label describing the contents of the container and providing indications and/or instructions regarding use of the contents of the container for controlling bleeding in a mammal. In yet another embodiment, the aforementioned kit is provided wherein the container is a vial or bottle or prefilled syringe.

DETAILED DESCRIPTION OF THE INVENTION

It is to be understood that this invention is not limited to the FVII moieties described herein. It is one aspect of the present invention that relates to a proteinaceous construct comprising one member of the blood coagulation cascade, plasmatic (i.e., plasma-derived) and/or recombinant FVIIa or biologically active derivatives thereof (in the following also designated as "PSA-FVIIa-conjugate"), said FVII or said biologically active derivatives thereof being bound to one to four sialic acid moieties, wherein the in vivo-half-life of said FVIIa or said biologically active derivatives thereof is prolonged in the blood of a mammal. As used herein, the term "proteinaceous construct" refers to an activated factor VII (FVIIa) molecule selected from the group consisting of plasmatic FVIIa, recombinant FVIIa (rFVIIa), and a biologically active derivative of FVIIa; and (b) at least one physiologically acceptable carbohydrate moiety comprising 1-4 sialic acid units bound to said FVIIa molecule. As used herein, the term "plasmatic" refers to "plasma derived."

FVIIa Polypeptides and Polynucleotides

The FVIIa molecules useful for the present invention include the full-length protein, precursors of the protein, biologically active or functional subunits or fragments of the protein, and functional derivatives thereof. Reference to FVIIa is meant to include all potential forms of such proteins.

According to the present invention, the term "recombinant Factor VIIa" (rFVIIa) does not underlie a specific restriction and may include any rFVIIa, heterologous or naturally occurring, obtained via recombinant DNA technology, or a biologically active derivative thereof. In certain embodiments, the term encompasses proteins and nucleic acids, e.g., gene, pre-mRNA, mRNA, and polypeptides, polymorphic variants, alleles, mutants, and interspecies homologs that: (1) have an amino acid sequence that has greater than about 60% amino acid sequence identity, 65%, 70%, 75%, 80%, 85%, 90%, 91%, 92%, 93%, 94%, 95%, 96%, 97%, 98% or 99% or greater amino acid sequence identity, over a region of at least about 25, 50, 100, 200, 300, 400, or more amino acids (up to the full length sequence of 406 amino acids for the mature protein), to a polypeptide encoded by a referenced nucleic acid or an amino acid sequence described herein; (2) specifically bind to antibodies, e.g., polyclonal antibodies, raised against an immunogen comprising a referenced amino acid sequence as described herein immunogenic fragments thereof, and conservatively modified variants thereof; (3) specifically hybridize under stringent hybridization conditions to a nucleic acid encoding a referenced amino acid sequence as described herein, and conservatively modified variants thereof, (4) have a nucleic acid sequence that has greater than about 95%, greater than about 96%, 97%, 98%, 99%, or higher nucleotide sequence identity, over a region of at least about 25, 50, 100, 150, 200, 250, 500, 1000, or more nucleotides (up to the full length sequence of 1218 nucleotides of the mature protein), to a reference nucleic acid sequence as described herein.

As used herein, "endogenous FVIIa" includes FVIIa which originates from said mammal. It also includes FVIIa transcribed from a transgene or any other foreign DNA present in said mammal. As used herein, "exogenous FVIIa" includes FVIIa which does not originate from said mammal.

Variant (or analog) polypeptides include insertion variants, wherein one or more amino acid residues supplement an FVIIa amino acid sequence. Insertions may be located at either or both termini of the protein, or may be positioned within internal regions of the FVIIa amino acid sequence. Insertion variants, with additional residues at either or both termini, can include for example, fusion proteins and proteins including amino acid tags or labels. For example, the FVIIa molecule may optionally contain an N-terminal Met, especially when the molecule is expressed recombinantly in a bacterial cell such as E. coli.

In deletion variants, one or more amino acid residues in a FVIIa polypeptide are removed. Deletions can be effected at one or both termini of the FVIIa polypeptide, or with removal of one or more residues within the FVIIa amino acid sequence. Deletion variants, therefore, include all fragments of a FVIIa polypeptide sequence.

In substitution variants, one or more amino acid residues of a FVIIa polypeptide are removed and replaced with alternative residues. In one aspect, the substitutions are conservative in nature and conservative substitutions of this type are well known in the art. Alternatively, the invention embraces substitutions that are also non-exemplary conservative. Exemplary conservative substitutions are described in Lehninger, [Biochemistry, 2nd Edition; Worth Publishers, Inc., New York (1975), pp. 71-77] and set out low.

Conservative Substitutions

| SIDE CHAIN CHARACTERISTIC | AMINO ACID |
|---|---|
| Non-polar (hydrophobic): | |
| A. Aliphatic | A L I V P |
| B. Aromatic | F W |
| C. Sulfur-containing | M |
| D. Borderline | G |
| Uncharged-polar: | |
| A. Hydroxyl | S T Y |
| B. Amides | N Q |
| C. Sulfhydryl | C |
| D. Borderline | G |
| Positively charged (basic) | K R H |
| Negatively charged (acidic) | D E |

Alternatively, exemplary conservative substitutions are set out immediately below.

Conservative Substitutions II

| ORIGINAL RESIDUE | EXEMPLARY SUBSTITUTION |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention can be recombinant molecules (e.g., heterologous and encoding the wild type sequence or a variant thereof, or non-naturally occurring). Reference polynucleotide and polypeptide sequences include, e.g., GenBank Accession Nos. J02933 for the genomic sequence, M13232 for the cDNA (Hagen et al. PNAS 1986; 83: 2412-6), ad P08709 for the polypeptide sequence (references incorporated herein in their entireties). A variety of polymorphisms of FVII have been described, for example see Sabater-Lleal et al. (Hum Genet. 2006; 118:741-51) (reference incorporated herein in its entirety).

As used herein "biologically active derivative" or "biologically active variant" includes any derivative or variant of a molecule having substantially the same functional and/or biological properties of said molecule, such as binding properties, and/or the same structural basis, such as a peptidic backbone or a basic polymeric unit.

As used herein, "plasma-derived FVIIa" or "plasmatic" includes all forms of the protein found in blood obtained from a mammal having the property of activating the coagulation pathway.

As used herein, "recombinant FVIIa" includes rFVIIa obtained via recombinant DNA technology. It may be produced by any method known in the art. One specific example is disclosed in U.S. Pat. No. 4,784,950. An example of such rFVIIa is NovoSeven manufactured and sold by Novo Nordisk.

FVIIa Production and Expression

The production of rFVIIa may include any method known in the art for (i) the production of recombinant DNA by genetic engineering, e.g. via reverse transcription of RNA and/or amplification of DNA, (ii) introducing recombinant DNA into procaryotic or eucaryotic cells by transfection, e.g. via electroporation or microinjection, (iii) cultivating said transformed cells, e.g. in a continuous or batchwise manner, (iv) expressing rFVIIa, e.g. constitutively or upon induction, and (v) isolating said FVIIa, e.g. from the culture medium or by harvesting the transformed cells, in order to (vi) obtain purified rFVIIa, e.g. via anion exchange chromatography or affinity chromatography.

The rFVIIa can be produced by expression in a suitable prokaryotic or eukaryotic host system characterized by producing a pharmacologically acceptable rFVIIa molecule. Examples of eukaryotic cells are mammalian cells, such as CHO, COS, HEK 293, BHK, SK-Hep, and HepG2. There is no particular limitation to the reagents or conditions used for producing or isolating rFVIIa according to the present invention and any system known in the art or commercially available can be employed.

A wide variety of vectors can be used for the preparation of the rFVIIa and can be selected from eukaryotic and prokaryotic expression vectors. Examples of vectors for prokaryotic expression include plasmids such as pRSET, pET, pBAD, etc., wherein the promoters used in prokaryotic expression vectors include lac, tre, tip, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

Sialic Acid

As used herein, "sialic acid moieties" includes sialic acid monomers or polymers which are soluble in an aqueous solution or suspension and have no negative impact, such as side effects, to mammals upon administration of the PSA-FVIIa-conjugate in a pharmaceutically effective amount. There is no particular limitation to the sialic acid unit used according to the present invention. The polymers are characterized, in one aspect, as having from 1 to 4 units. Different sialic acids units can be also combined in a chain.

Sialic acid moieties can be bound to FVIIa for example by the method described in U.S. Pat. No. 4,356,170, which is herein incorporated by reference. In one embodiment of the invention the polysaccharide compound may be a naturally occurring polysaccharide, a derivative of a naturally occurring polysaccharide, or a naturally occurring polysaccharide derivative. Generally, all of the saccharide residues in the compound are sialic acid residues. The polysaccharide MW suitably is within about 2,000-100,000 for best coupling and antigenicity.

Other techniques for coupling PSA to polypeptides are also known. For example, US Publication No. 2007/0282096 describes conjugating an amine or hydrazide derivative of, e.g., PSA, to proteins. In addition, US Publication No. 2007/0191597 describes PSA derivatives containing containing an aldehyde group for reaction with substrates (e.g., proteins) at the reducing terminal end.

In one embodiment of the invention, the polysialic acid portion of the polysaccharide compound is highly hydrophilic, and in another embodiment the entire compound is highly hydrophilic. Hydrophilicity is conferred primarily by the pendant carboxyl groups of the sialic acid units, as well as the hydroxyl groups. The saccharide unit may contain other functional groups, such as, amine, hydroxyl or sulphate groups, or combinations thereof. These groups may be present on naturally occurring saccharide compounds, or introduced into derivative polysaccharide compounds.

Polysaccharide compounds of particular use for the invention are those produced by bacteria. Some of these naturally occurring polysaccharides are known as glycolipids. It is particularly advantageous if the polysaccharide compounds are substantially free of terminal galactose units, which tend to be recognized by galactose receptors of hepatocytes and Klupffer cells.

Linkage

FVIIa may be covalently linked to the polysaccharide compounds by any of various techniques known to those of skill in the art. Various examples are identified at column 7, line 15, through column 8, line 5 of U.S. Pat. No. 5,846,951.

Examples include linkage through the peptide bond between a carboxyl group on one of either the FVIIa or polysaccharide and an amine group of the other, or an ester linkage between a carboxyl group of one and a hydroxyl group of the other. Another linkage by which the active ingredient, e.g., FVIIa, could be covalently bonded to the polysaccharide compound is via a Schiff base, between a free amino group on the active ingredient being reacted with an aldehyde group formed at the non-reducing end of the polymer by periodate oxidation (Jennings and Lugowski, J. Immunol. 1981; 127:1011-8; Femandes and Gregonradis, Biochim Biophys Acta. 1997; 1341; 26-34). The generated Schiff Base can be stabilized by specific reduction with $NaCNBH_3$ to form a secondary amine. An alternative approach is the generation of terminal free amino groups in the polysialic acid (PSA) by reductive amination with $NH_4Cl$ after prior oxidation. Bifunctional reagents can be used for linking two amino or two hydroxyl groups. For example PSA containing an amino group can be coupled to amino groups of the protein with reagents like $BS^3$ (Bis(sulfosuccinimidyl)suberate/Pierce, Rockford, Ill.). In addition heterobifunctional cross linking reagents like Sulfo-EMCS (N-ε-Maleimidocaproyloxy) sulfosuccinimide ester/Pierce) can be used for instance to link amine and thiol groups.

In another approach, a PSA hydrazide can be prepared and coupled to the carbohydrate moiety of the protein after prior oxidation and generation of aldehyde functions.

A free amine group of the therapeutic protein may be reacted with the 1-carboxyl group of the sialic acid residue to form a peptidyl bond or an ester linkage can be formed between the 1-carboxylic acid group and a hydroxyl or other suitable active group on an active ingredient. Alternatively, a carboxyl group may form a peptide linkage with deacetylated 5-amino group. An aldehyde group of a molecule of a pharmaceutically active compound may form a Schiff base with the N-deacetylated 5-amino group of a sialic acid residue.

Alternatively, the polysaccharide compound may be associated in a non-covalent manner with the pharmaceutically active compound, e.g., FVIIa. For example the polysaccharide compound and the pharmaceutically active compound may be linked via hydrophobic interactions, for example via lipid components of the polysaccharide compound with a hydrophobic pharmaceutically active compound. Other non-covalent associations may be via electrostatic interactions, with oppositely charged ions attracting each other.

The pharmaceutically active compound may be directly covalently linked to the polysaccharide compound in stoichiometric amounts (e.g., 1:1). Alternatively, two or more molecules of polysaccharide compound may be linked to one molecule of active ingredient.

Use

The present invention is directed to increasing in vivo half-life of blood coagulation proteins, especially FVIIa or biologically active derivatives thereof having a bleeding disorder associated with functional defects or deficiencies of FVIIa as compared to the in vivo half-life of FVIIa not linked to at least one physiologically acceptable sialic acid moiety. The PSA-FVIIa-conjugate of the present invention can further be used for the treatment of bleeding disorders associated with functional defects or congenital or acquired deficiencies of at least one of FVIII and FIX.

According to the state of the art in therapy and according to international guidelines and regulations, the pharmacokinetics of infused FVIIa are recognized and accepted as valid surrogate markers for efficacy (Björkman and Berntrop, Clin Pharmacokinet. 2001; 40:185-32).

This is based on the validated assumption that an infused FVIIa product which had been characterized by standardized tests for functional activity will be found in the blood stream and will act there as expected as a component of the coagulation cascade. Therefore any pharmacokinetic analysis in animal models will be predictive for efficacy expected in patients treated with FVIIa products.

Half-Life

In one embodiment of the present invention, the in vivo half-life of the proteinaceous construct is prolonged. In a related embodiment, the in vivo half-life of the proteinaceous construct is prolonged by at least a factor of two, while in another embodiment the in vivo half-life is prolonged by at least a factor of three, as compared to FVIIa which is not bound to sialic acid. The prolonging of FVIIa half-life can be assessed by measuring the pharmacokinetics in rats, as described in the examples below.

Administration

The route of administration does not exhibit particular limitations, and in one embodiment the proteinaceous construct of the present invention may be administered by injection, such as intravenous, intramuscular, or intraperitoneal injection.

To administer compositions comprising a proteinaceous construct of the present invention to human or test animals, in one aspect, the compositions comprise one or more pharmaceutically acceptable carriers. The terms "pharmaceutically" or "pharmacologically acceptable" refer to molecular entities and compositions that are stable, inhibit protein degradation such as aggregation and cleavage products, ad in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

As used herein, "effective amount" includes a dose suitable for treating a mammal having a bleeding disorder as outlined above.

The compositions may be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and or surgical implantation at a particular site is contemplated as well. Generally, composition are essentially free of pyrogens, as well as other impurities that could be harmful to the recipient.

Single or multiple administrations of the compositions can be carried out with the dose levels and pattern being selected by the treating physician. For the prevention or treatment of disease, the appropriate dosage will depend on the type of disease to be treated, as described above, the severity and course of the disease, whether drug is administered for preventive or therapeutic purposes, previous therapy, the patient's clinical history and response to the drug, and the discretion of the attending physician.

Pharmaceutical Compositions

The present invention also relates to a pharmaceutical composition comprising an effective amount of a proteinaceous construct as defined above. The pharmaceutical composition may further comprise a pharmaceutically acceptable carrier, diluent, salt, buffer, or excipient. The pharmaceutical composition can be used for treating the above-defined bleeding disorders. The pharmaceutical composition of the invention may be a solution or a lyophilized product. There are many known methods of forming stable solution of proteins, and specifically FVIIa. One example is disclosed in U.S. Pat. No. 5,874,408. Solutions of the pharmaceutical composition may be subjected to any suitable lyophilization process.

Kits

As an additional aspect, the invention includes kits which comprise a composition of the invention packaged in a manner which facilitates its use for administration to subjects. In one embodiment, such a kit includes a compound or composition described herein (e.g., a composition comprising a proteinaceous construct), packaged in a container such as a sealed bottle or vessel, with a label affixed to the container or included in the packaged that describes use of the compound or composition in practicing the method. In one embodiment, the kit contains a first container having a composition comprising a proteinaceous construct and a second container having a physiologically acceptable reconstitution solution for the composition in the first container. In one aspect, the compound or composition is packaged in a unit dosage form. The kit may further include a device suitable for administering the composition according to a specific route of administration. Preferably, the kit contains a label that describes use of the therapeutic protein or peptide composition.

EXAMPLES

Figure 1:
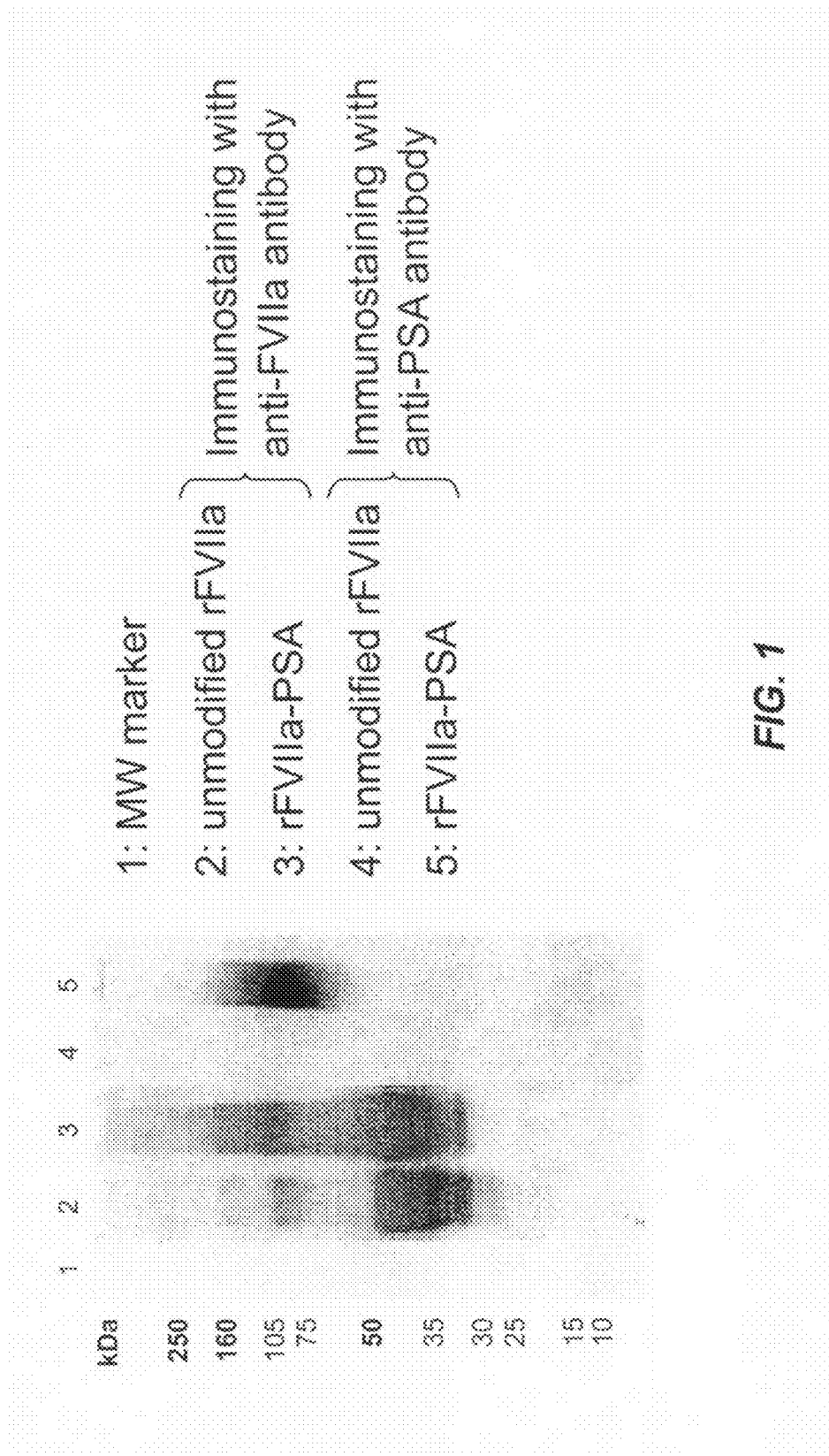
FIG. 1 shows a SDS-PAGE of rFVIIa after conjugation with PSA

Modification of Lysine Residues in rFVIIa with Colominic Acid

The modification of lysine residues with sialic acid (colominic acid, CA) was carried out as described by Jennings and Lugowski (J Immunol. 1981; 127; 1011-8). For this procedure CA from Sigma (Sigma-Aldrich, St. Louis; MO) was used. An aqueous solution of CA (concentration: 20 mg/mL) containing 0.1 M NaIO$_4$ was stirred for 15 mm in the dark at room temperature to oxidize the CA. Two mL ethylene glycol per mL of the activated CA solution was added and stirred for further 30 min in the dark at room temperature. The solution was dialyzed over night against 0.05 M sodium phosphate buffer, pH 7.2 in the dark at a temperature ranging from 2-8° C.

Subsequently an aliquot of this solution was added to a rFVIIa solution (30 µg/mL) in 0.05 M sodium phosphate buffer, pH 7.2 to give a final concentration of 100 mg activated CA per mg rFVIIa. This mixture was stirred for 180 min at room temperature in the dark. NaCNBH$_3$ was added (final concentration 10 mg/mg rFVIIa) and the mixture was incubated for 18 h at room temperature in the dark under gentle shaking. Then 2.5 mL of an aqueous 1 M TRIS-solution, pH 7.2 was added per mL of this mixture and stirred for 60 min to terminate the reaction.

The free reagents were separated from the rFVIIa-CA acid conjugate by ion exchange chromatography using a QHyperD F 50 μm resin (Pall BioSepra, Cergy, France) and a Pharmacia XK-10 column (Pharmacia XK 10; h=15 cm). The CA conjugated protein was eluted with elution buffer (20 mM HEPES/1 M NaCl, pH 8.0) In a final step the eluate was concentrated by ultrafiltration/diafiltration (UF/DF) using a 30 kD membrane (regenerated cellulose/Millipore) against 20 mM HEPES buffer, pH 7.4 containing 150 mM NaCl and 0.5% sucrose.

Example 2

Biochemical Characterization of Polysialylated rFVIIa

The enzymatic activity of rFVIIa-PSA was determined by a clotting assay, where FVIIa was added to a human FVII-deficient plasma and the clotting was triggered by a truncated tissue factor reacting with FVIIa but not with FVII (Staclot, Diagnostica Stago, Asnières, France).

The FVIII-bypassing activity of rFVII-PSA was measured by a thrombin generation assay (TGA), where FVIIa was added to a severe haemophilia A plasma, containing a high titer of anti-FVIII inhibitor in the presence of a thrombin-specific fluorescence peptide-substrate. Coagulation was triggered with a tissue factor-phospholipid complex and thrombin generation was continuously measured by the cleavage rate of the fluorophore of the substrate. The thrombin generation activity was calculated from the peak thrombin, i.e. the maximum thrombin concentration observed during the assay. In both cases a NovoSeven recombinant FVIIa preparation (Novo Nordisk, Copenhagen, Denmark) was used as reference.
As seen in Table 1 the specific activity of PSA-rFVIIa decreased after the modification.

TABLE 1

Specific activity of rFVIIa before and after conjugation with PSA

| | FVIIa activity | |
| --- | --- | --- |
| | STF (U/mg protein) | TGA (U/mg protein) |
| unmodified rFVIIa | 45942 | 44296 |
| rFVIIa-PSA | 1003 | 22 |

Modification was visualized by SDS-PAGE performed under non-reducing conditions. Immunostaining was done with a polyclonal anti-FVII antibody (Affinity Biologicals; Ancaster, Canada) and with a monoclonal anti-PSA antibody (Chemicon International, Temecula, Calif., USA). Modification resulted in an increase of the MW of FVIIa demonstrated by a smeared area correlating with the PSA-containing protein (FIG. 1).

Example 3

Pharmacokinetic of rFVIIa-PSA-Conjugate in Rats

Four rats (Crl:CD(SD), Charles River Laboratories, Wilmington, Mass.) were anaesthetized and rFVIIa-PSA-conjugate (16.500 U FVIIa/kg) in buffer (1.3 g/L glycylglycine, 3 g/L sodium chloride, 30 g/L mannitol, 1.5 g/L $CaCl_2.\times 2H_2O$, 0.1 g/L Tween 80, pH 5.5) was applied by intravenous injection into the tail vein in a volume dose of 20 mL per kg. Unmodified rFVIIa in a dose of 18.000 U FVIIa/kg was used as control in 6 normal rats. Blood samples were taken from retrobulbary venous plexus 5 min, 30 min, 1 h, 2, 4, 6, 8 and 24 h after substance application, citrate plasma was prepared and frozen for further analysis.

Figure 2:
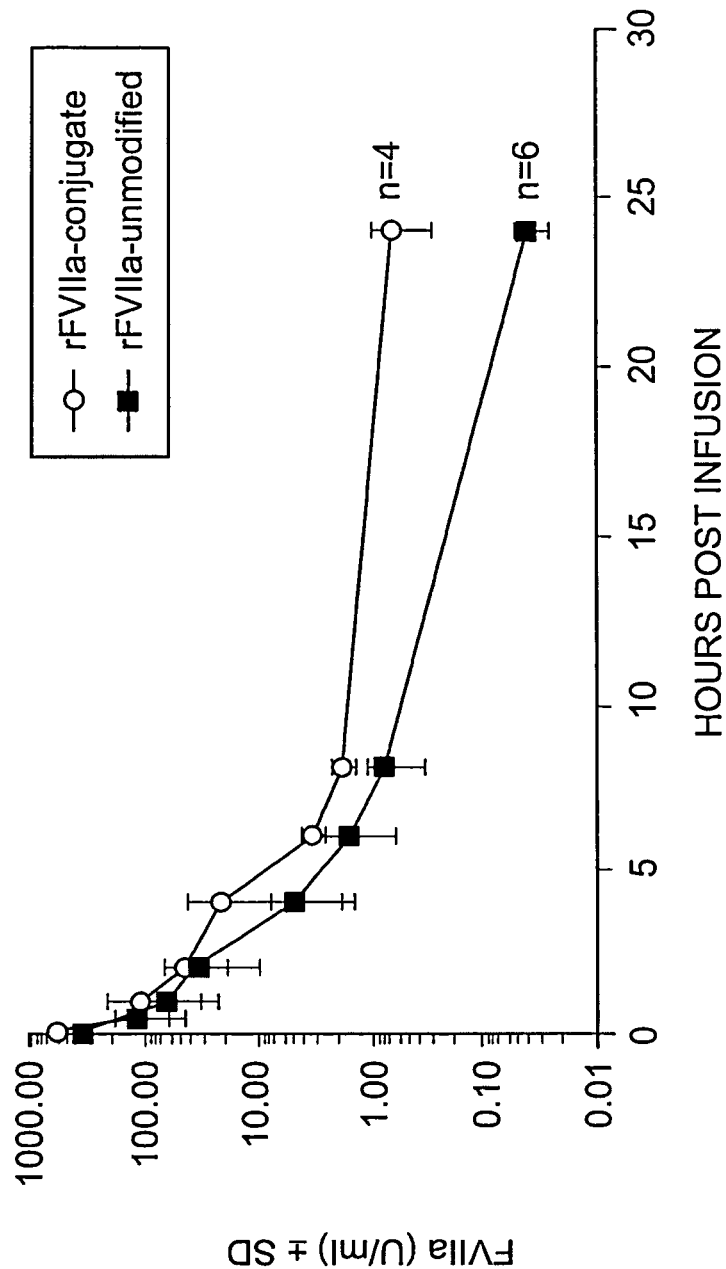
FIG. 2 shows the pharmacokinetics of rFVIIa-PSA-conjugate and unmodified rFVIIa in rats

Then the FVIIa activity (Staclot, Diagnostica Stago, Asnières, France) in plasma was measured. Half life of unmodified rFVIIa was 1.1 h and was increased to 2.3 h with the rFVIIa-conjugate (FIG. 2).

Figure 3:
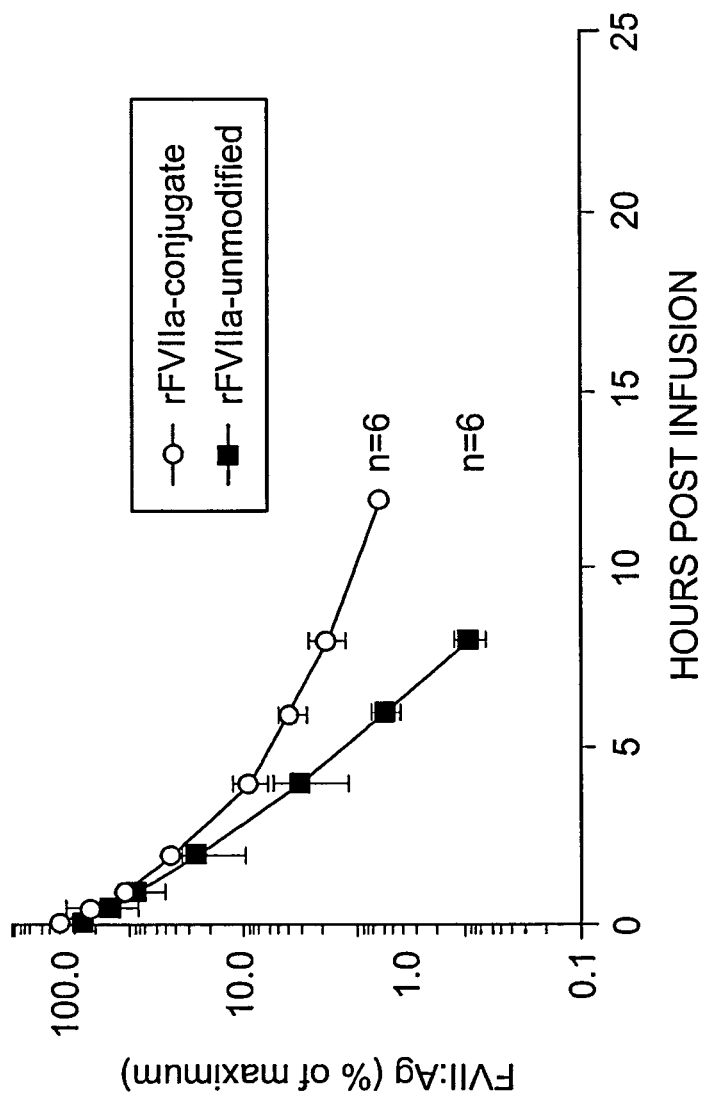
FIG. 3 shows the pharmacokinetics of rFVIIa-PSA-conjugate and unmodified rFVIIa in rats (antigen level)

The pharmacokinetics of FVIIa antigen levels were measured in an additional experiment. Six rats were anaesthetized and rFVIIa-PSA-conjugate (450 μg/kg) in buffer (1.3 g/L glycylglycine, 3 g/L sodium chloride, 30 g/L mannitol, 1.5 g/L $CaCl_2.2H_2O$, 0.1 g/L Tween 80, pH 5.5) was applied by intravenous injection into the tail vein in a volume dose of 10 mL per kg. Unmodified rFVIIa in a dose of 390 μg/kg was used as control in 6 rats. Blood samples were taken from retrobulbary venous plexus, 5 min, 30 min, 1, 2, 4, 6, 8, 12 and 24 h after substance application. Citrate plasma was prepared and frozen for further analysis. FVII antigen levels in plasma were measured with an ELISA (polyclonal anti-human FVII antibody). Half life calculation by linear regression as determined with MS Excel resulted in 1.1 h for native rFVIIa and 3.1 h for the rFVIIa-conjugate. Data for FVII antigen are normalized to the mean plasma level obtained 5 min after application (FIG. 3).

Example 4

N-Terminal Polysialylation of FVIIa

The conjugation of CA at the N-terminus of FVIIa was performed at pH 6.0. For this procedure CA from Sigma (Sigma-Aldrich) was used, which was further purified by anion-exchange chromatography on Q-Sepharose FF (GE Healthcare, Munich, Germany). An aqueous solution of purified CA (concentration: 23 mg/mL) containing 0.04 M $NaIO_4$ was stirred for 15 min in the dark at room temperature to oxidize the CA. Subsequently an aliquot of this solution was added to a rFVIIa solution (740 μg/mL) in 0.05 M sodium phosphate buffer, pH 6.0 to give a final concentration of 60 mg activated CA per mg rFVIIa (approx. 150 molar excess). This mixture was stirred for 180 min at room temperature in the dark. $NaCNBH_3$ was added (25 mg/mg rFVIIa) and the mixture was incubated for 24 h at 4° C. in the dark under gentle shaking. Then 2.5 mL of an aqueous 1 M TRIS-solution, pH 7.2 was added per mL of this mixture and stirred in the dark at 4° C. for 60 min to terminate the reaction.

The free reagents were separated from the rFVIIa-CA acid conjugate by ion exchange chromatography using a QHyperD F 50 μm resin (Pall BioSepra, Cergy, France) and a Pharmacia XK-16 column (Pharmacia XK 16; h=14 cm). Then the CA conjugated protein was eluted with elution buffer (20 mM HEPES/0.5M NaCl, pH 8.0). In a final step the eluate was concentrated by UF/DF using a 10 kD membrane (regenerated cellulose/Millipore) against 20 mM HEPES buffer, pH 7.4 containing 150 mM NaCl. The ion exchange chromatography and the UF/DF step were performed at 4° C.

The enzymatic activity of N-terminal modified rFVIIa-PSA was determined by a clotting assay and by a thrombin generation assay as described in Example 2. The results are summarized in Table 2.

TABLE 2

Specific activity of rFVIIa before and after N-terminal conjugation with PSA

| | FVIIa activity | |
|---|---|---|
| | STF (U/mg protein) | TGA (U/mg protein) |
| unmodified rFVIIa | 52749 | 56814 |
| rFVIIa-PSA - (N terminal) | 25030 | 12564 |

The specific activity of N-terminal conjugated PSA-rFVIIa decreased to approximately 50% as measured by the STF assay, and to 25% by TGA.

Figure 4:
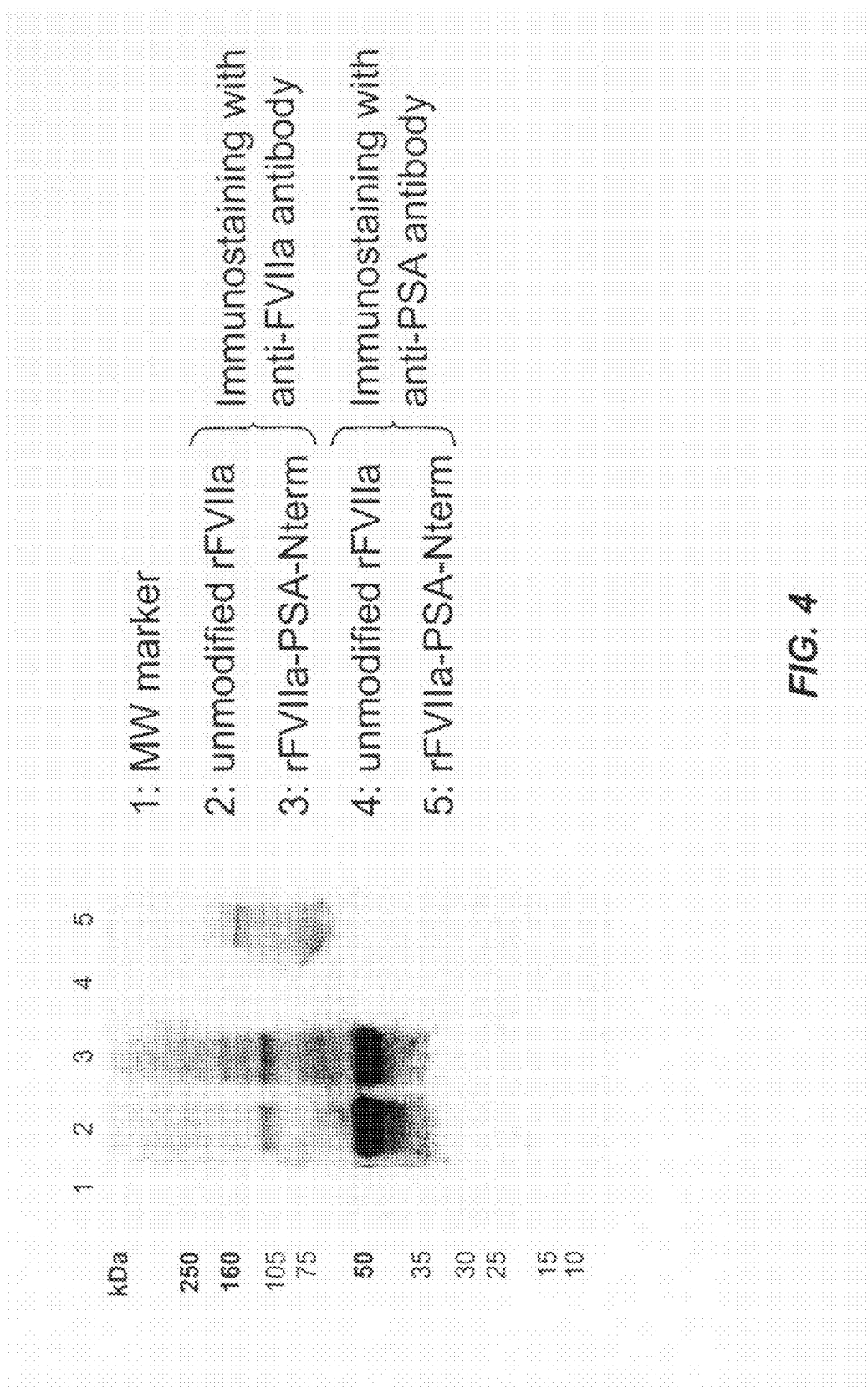
FIG. 4 shows a SDS-PAGE of rFVIIa after N-terminal conjugation with PSA.

Modification was visualized by SDS-PAGE performed under non-reducing, conditions developed by immunostaining with a polyclonal anti-FVII antibody and with a polyclonal anti-PSA antibody as described in Example 2. Modification resulted in a slight increase of the MW of FVIIa correlating with the bands shown in the anti-PSA-stained immunoblot (FIG. 4).

Example 5

Conjugation of FVIIa with CNBr Activated Synthetic N-Acetylneuraminic Acid

RFVIIa was conjugated with N-acetylneuraminic acid as described in U.S. Pat. No. 3,487,890. 350 mg synthetic N-acetylneuraminic acid (Sigma-Aldrich) were dissolved in 10 mL 0.1 M HEPES buffer, pH 9.0. Then 430 mg CNBr (Fluka, Steinhamm, Germany) were added to this solution and the pH was adjusted to 9.5 with 0.5 M NaOH during the activation procedure. After 30 min the pH value was 9.5. Then the pH value was adjusted to 8.4 by addition of 0.1 M HCl. During the whole activation procedure the temperature was controlled by use of an ice bath and kept at 20-25° C. For conjugation of the activated N-acetylneuraminic acid with rFVIIa a solution of rFVIIa (50 mL/0.44 mg rFVIIa mL) in 50 mM phosphate buffer, pH 7.2 was added and incubated under gentle stirring at room temperature for 30 min. Then 20 mL 0.2 M Tris-buffer were added for termination of the reaction and blocking of free cyanate esters and the mixture was incubated under gentle stirring for 15 in. Finally the solution was concentrated by UF/DF using a 10 kD membrane (regenerated cellulose/Millipore) against 50 mM phosphate buffer pH 7.2.

Example 6

Conjugation of FVIIa with CNBr Activated Synthetic N-Acetylneuraminic Acid Trimer RFVIIa was conjugated to a synthetic N-acetylneuraminic acid trimer obtained from TimTec, LLC (Newark, USA) as described in U.S. Pat. No. 3,487,890 for N-acetylneuraminic acid. 350 mg of the N-acetylneuraminic acid trimer were dissolved in 10 mL 0.1 M HEPES buffer, pH 9.0. Then 430 mg CNBr (Fluka) were added to this solution and the pH was adjusted to 9.5 with 0.5 M NaOH during the activation procedure. After 30 min the pH value was at 9.5. The pH value was adjusted to 8.4 by addition of 0.1 M HCl. During the whole activation procedure the temperature was controlled by use of an ice bath and kept at 20-25° C. Then the conjugation of the activated trimer with FVIIa was performed as described in Example 5.

Example 7

Biochemical Characterization of Mono-SA-FVIIa and Tri-SA-FVIIa

The enzymatic activity of modified rFVIIa-conjugated to N-acetylneuraminic acid (Mono-SA) described in Example 5 or N-acetylneuraminic acid trimer (Tri-SA) described in Example 6 was determined by a clotting assay and by a thrombin generation assay as described in Example 2. The results are summarized in Table 3.

TABLE 3

Specific activity of rFVIIa before and after N-terminal conjugation with PSA

| | FVIIa activity | |
|---|---|---|
| | STF (U/mg protein) | TGA U/mg protein) |
| unmodified rFVIIa | 40579 | 57230 |
| Mono-SA-rFVIIa | 6064 | 21784 |
| Tri-SA-rFVIIa | 1743 | 4131 |

The specific activity of the oligo-PSA conjugated rFVIIa decreased as measured by the STF assay, but the mono-SA-rFVIIa retained about 50% of its FVIII-bypassing activity, measured by TGA.

Figure 5:
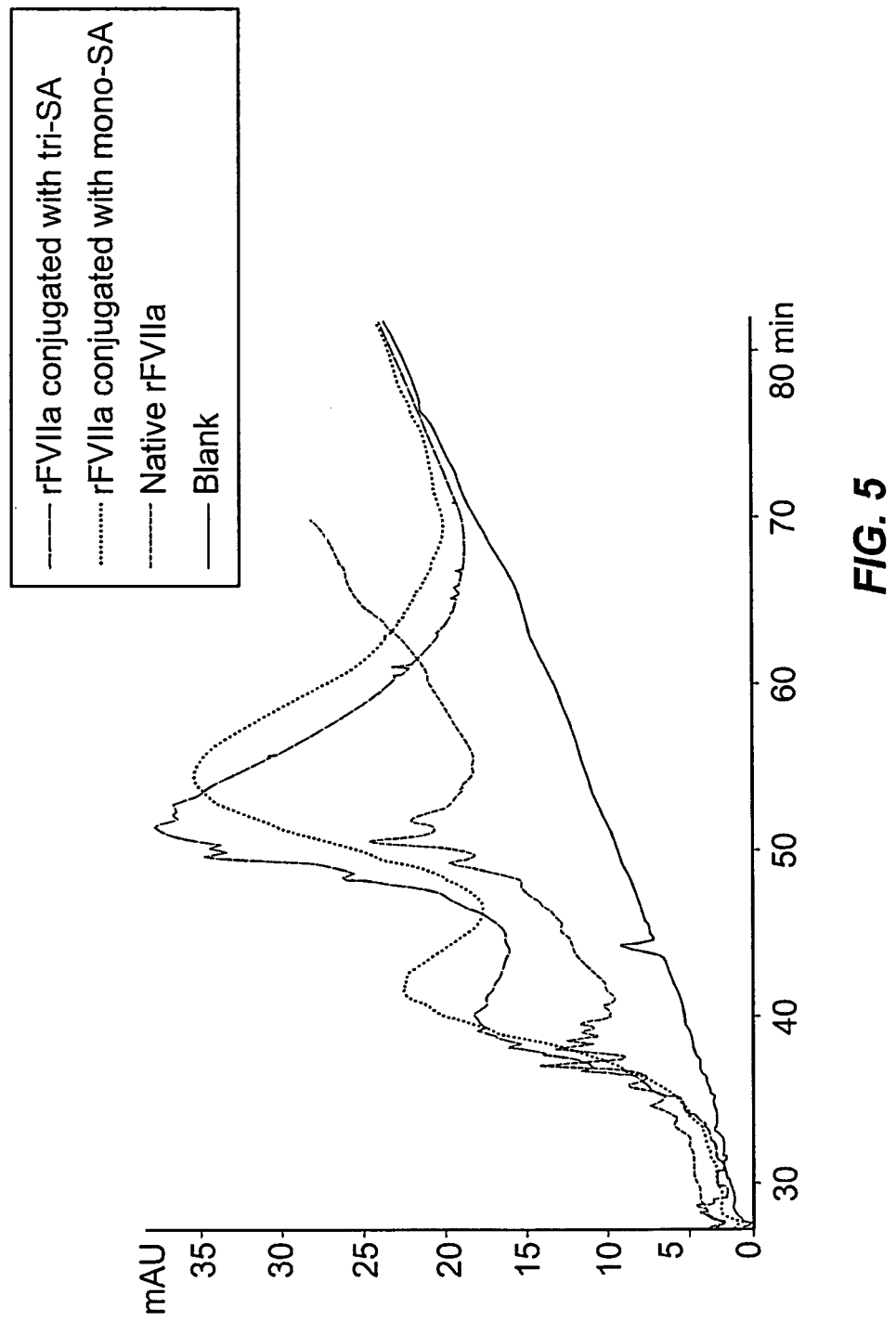
FIG. 5 shows a capillary electrophoresis of mono-SA rFVIIa and Tri-SA-rFVIIa.

In addition Mono-SA rFVIIa and Tri-SA-rFVIIa were investigated by capillary electrophoresis (CE) as described by Klausen and Kornfelt (J Chromatogr A. 1995; 718:195-202). The results are illustrated in FIG. 5. A clear shift to higher retention times of the Mono-SA rFVIIa and Tri-SA-rFVIIa due to additional negative charges in comparison to the native rFVIIa is indicated.

Example 8

Pharmacokinetics of rFVIIa-Mono SA and rFVIIa-Tri SA Conjugate in Rats

Figure 6A:
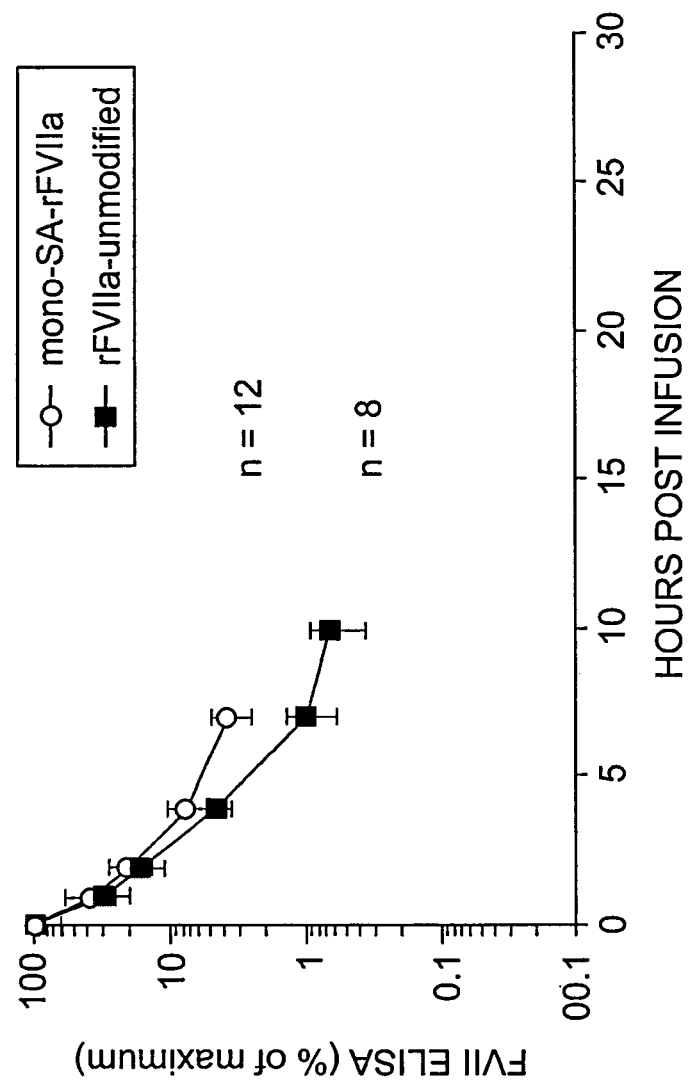
FIGS. 6 A and B show the pharmacokinetics of rFVIIa-PSA-conjugates and unmodified rFVIIa in rats, A: mono-SA-rFVIIa, B: tri-SA-rFVIIa
Figure 6B:
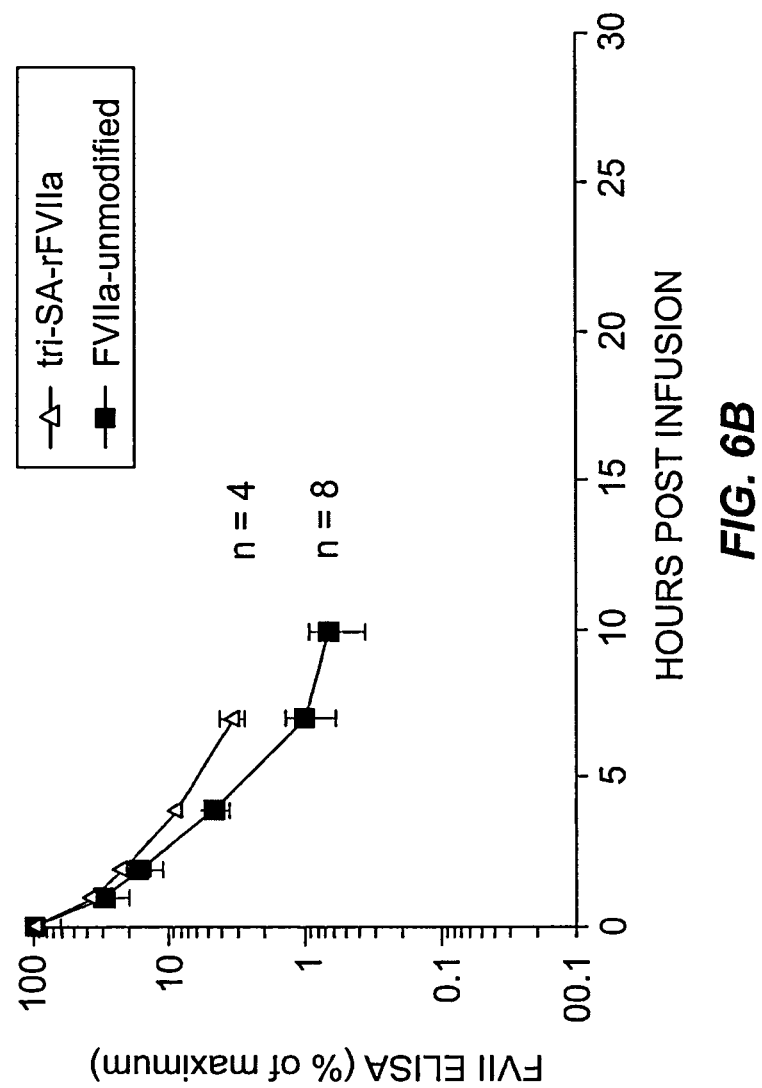

Twelve rats were anaesthetized and rFVIIa-mono SA-conjugate (400 μg protein/kg) in buffer (1.3 g/L glycylglycine, 3 g/L sodium chloride, 30 g/L mannitol, 1.5 μL $CaCl_2.2H_2O$, 0.1 g/L Tween 80, pH 5.5) was applied by intravenous injection into the tail vein in a volume dose of 10 mL per kg. Four rats were treated with rFVIIa-tri SA-conjugate (400 μg protein/kg). Unmodified rFVIIa in a dose of 400 μprotein/kg was used as control in 8 normal rats. Blood samples were taken from retrobulbary venous plexus, 5 min, 30 min, 1, 2, 4, 7, 10 and 22 h after substance application, citrate plasma was prepared and frozen for further analysis. FVII antigen levels in plasma were measured with an ELISA (polyclonal anti-human FVII antibody). Data were normalized relative to the concentration, found in plasma 5 min after application. 7 h after application, the plasma levels for rFVIIa-mono-SA and tri-SA-rFVIIa were higher than for the native rFVIIa control. The results are illustrated in FIG. 6A (rFVIIa-mono SA) and FIG. 6B (rFVIIa-tri SA).

Example 9

Coupling of N-Acetylneuraminic Acid Trimer to rFVIIa by Reductive Amination

The conjugation of rFVIIa with N-acetylneuraminic acid trimer by reductive amination was carried out as described by Biessen et al. (Biochem J 1994; 299:291-6). 350 mg N-acetylneuraminic acid trimer (TimTec) were dissolved in 10 mL 0.1 M HEPES buffer, pH 7.0 and added to 32 mL of a solution of recombinant FVIIa in 20 mM HEPES, 70 mm NaCl, pH 7.4 (0.3 mg/mL). Then $NaCNBH_3$ was added to give a final concentration of 50 mg/mL and the pH was corrected to pH 7.0 by addition of 0.1 M HCl. The mixture was incubated at 37° C. under gentle stirring for 48 h. The solution was concentrated by UF/DF using a 10 kD membrane (regenerated cellulose/Millipore) against 20 mM Hepes buffer, 150 mM NaCl, pH 7.4.

Figure 7:
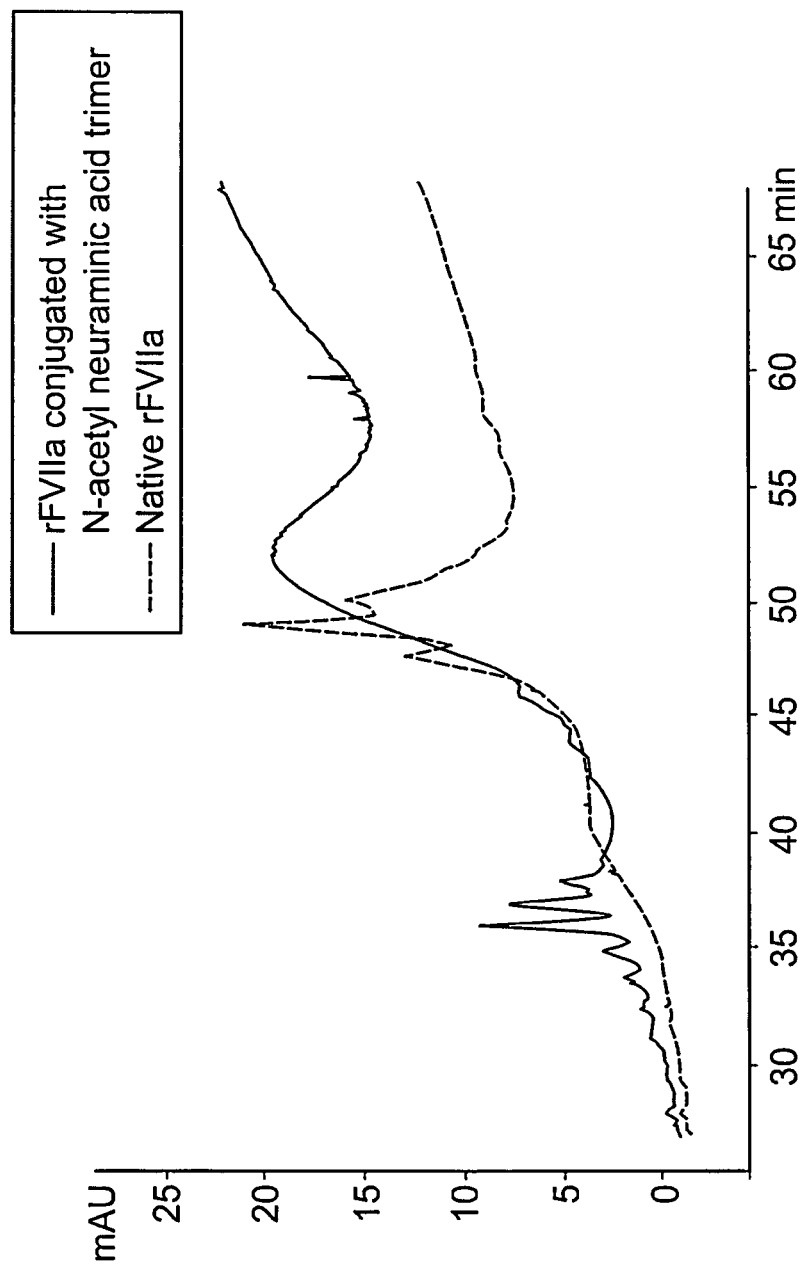
FIG. 7 shows a capillary electrophoresis of N-acetylneuraminic acid trimer The present invention will be further illustrated in the following examples, without any limitation thereto.

The conjugation of the N-acetylneuraminic acid trimer to the rFVIIa was shown by CE performed according to Klausen and Kornfelt (J Chromatogr A. 1995, 718:195-2027). The results are indicated in FIG. 7. A clear shift of the derivative to higher retention times in comparison to the native rFVIIa is indicated.

Example 10

Purification and Derivatization of Colominic Acid

CA was purified by of anion-exchange chromatography on Q-Sepharose FF as described in WO0601616A1. Five g CA were dissolved in 50 mL 10 mM Triethanolamine buffer, pH 7.4 containing 25 mM NaCl (=starting buffer). This solution was applied onto a Pharmacia XK50 column filled with Q-Sepharose FF (GE Healthcare), which was equilibrated with starting buffer. Then the column was washed with 8 column volumes (CV) starting buffer and the bound CA was eluted stepwise with 3CV 200 mM NaCl, 350 mM NaCl and 500 mM NaCl in starting buffer. The fraction eluted with 350 mM NaCl showed a molecular weight of 20 kDa as indicated by SDS gel electrophoresis. This fraction was concentrated by ultrafiltration using a 5 kD membrane made of regenerated cellulose (Millipore) and subsequently diafiltrated against 50 mM phosphate buffer, pH 7.2. Then the CA was oxidized with $NaIO_4$ as described in Example 1 and a terminal primary amino group was introduced by reductive amination as described in WO05016973A1. For reductive amination 11 mL of a 2 M $NH_4Cl$-solution were added to 20 mL of a solution containing 58 mg oxidized PSA/ml in 50 mM phosphate buffer, pH 7.2. Then a solution of 5M $NaCNBH_3$ in 1M NaOH was added to give a final concentration of 75 mM. The reaction was performed for 5 d at room temperature at pH 8.0. Then the mixture was dialyzed against a $(H_4)_2CO_3$ solution (50 mg/L) containing 10 mM NaCl and subsequently against 50 mM phosphate buffer, ph 8.0, containing 5 mM EDTA. Then a sulfhydryl group was introduced by reaction of the terminal primary amino group with 2-iminothiolane (Traut's reagent f Pierce). The reaction was carried out in 50 mM phosphate buffer, pH 8.0, containing 5 mM EDTA with 20 fold molar excess of reagent for 1 h at room temperature. Finally the PSA solution containing a terminal free SR group was subjected to ultrafiltration/diafiltration using a membrane with a cut-off of 5 kD and made of regenerated cellulose (Millipore).

Example 11

Coupling of PSA to rFVIIa by Use of a Heterobifunctional Cross-Linker

PSA (Sigma-Aldrich) was putrefied by anion-exchange chromatography on Q-Sepharose FF (GE-Healthcare) and a terminal sulfhydryl-group was introduced by chemical modification to form PSA-S as described in Example 10. For coupling of PSA-SH to rFVIIa the heterobifunctional, water soluble cross-linker Sulfo-EMCS ((N-ε-Maleimidocaproyloxy) sulfosuccinimide ester/Pierce) was used, containing two reactive groups: a maleimide group for conjugation to SH-groups and a sulfo-NHS-ester group for conjugation to free amino groups. To 2 mL of a rFVIIa solution (1.6 mg/mL) in 20 mM HEPES buffer, pH 7.4 containing 150 mM NaCl Sulfo-EMCS was added to give a final concentration of 0.07 mg cross linker/mg protein). The reaction was carried out for 30 min at room temperature. Subsequently 130 mg PSA-SH (100 fold excess) prepared according to Example 10 was added and the coupling reaction of the intermediate linker/rFVIIa complex to the PSA-SH was performed for additional 2 h at room temperature. Then the mixture was purified by HIC chromatography on Butyl-Sepharose (GE-Healthcare). A 5 M NaCl solution was added to the mixture to give a final concentration of 3M NaCl. Then this mixture was applied to the column filled with Butyl-Sepharose (GE-Healthcare) and the elution of the rFVIIa-PSA conjugate was carried out with 50 mM HEPES-buffer, pH 7.4, containing 6.7 mM $CaCl_2$. After elution of the conjugate the pH was adjusted to pH 6.9.

Example 12

Conjugation of PSA-Hydrazide to the Carbohydrate Moiety of rFVIIa

For conjugation of PSA to the carbohydrate moiety of rFVIIa a solution of rFVIIa in 20 mM HEPES buffer, pH 6.0 (1.6 mg/mL) is prepared. To 9 volumes of this solution 1 volume of a 5 mM $NaIO_4$-solution is added and gently mixed. The oxidation reaction is carried out for 1 h at 4° C. in the dark to generate free aldehyde groups. Then sodium bisulfite (final concentration 5 mM) is added to stop the reaction. Subsequently PSA-hydrazide (WO2006016168 A2) is added (final concentration 10 mM) and the coupling reaction to the aldehyde groups is performed for 1 h at room temperature. Then the PSA-rFVIIa conjugate is purified by anion-exchange chromatography on QHyperD (Pall BioSepra) as described in Example 1.

The invention claimed is:
1. A chemically-modified activated factor VII (FVIIa) molecule comprising,
   (a) a FVIIa molecule selected from the group consisting of plasmatic FVIIa and recombinant FVIIa (rFVIIa); and
   (b) at least one chain of 1-4 sialic acid units, each chain covalently bound to a separate amino acid residue of said FVIIa molecule;
   wherein the in vivo half-life of said chemically-modified FVIIa molecule is prolonged in the blood of a mammal as compared to the in vivo half-life of a FVIIa molecule that is not chemically modified.
2. A chemically-modified FVIIa molecule comprising,
   (a) a FVIIa molecule selected from the group consisting of plasmatic FVIIa and recombinant FVIIa (rFVIIa); and
   (b) at least one polysialic acid chain comprising a molecular weight of 2,000 to 100,000, each chain covalently linked directly to a separate amino acid residue of said FVIIa molecule;
   wherein the in vivo half-life of said chemically-modified FVIIa molecule is prolonged in the blood of a mammal as compared to the in vivo half-life of a FVIIa molecule that is not chemically modified.
3. A chemically-modified FVIIa molecule comprising:
   (a) a FVIIa molecule selected from the group consisting of plasmatic FVIIa and recombinant FVIIa (rFVIIa); and

(b) at least one polysialic acid chain comprising a molecular weight of at least 20,000, each chain bound to a separate oxidized carbohydrate moiety on said FVIIa;

wherein the in vivo half-life of said chemically-modified FVIIa molecule is prolonged in the blood of a mammal as compared to the in vivo half-life of a FVIIa molecule that is not chemically modified.

4. The chemically-modified FVIIa molecule of any one of claim 1, 2 or 3 wherein the in vivo half-life of said chemically-modified FVIIa molecule is increased by at least a factor of about two as compared to the in vivo half-life of a FVIIa molecule that is not chemically modified.

5. The chemically-modified FVIIa molecule of any one of claim 1, 2 or 3 wherein the in vivo half-life of said chemically-modified FVIIa molecule is increased by at least a factor of about three as compared to the in vivo half-life of a FVIIa molecule that is not chemically modified.

6. A pharmaceutical composition comprising an effective amount of the chemically-modified FVIIa molecule of any one of claim 1, 2 or 3, and one or more compounds selected from the group consisting of a pharmaceutically acceptable carrier, diluent, salt, buffer, and excipient.

7. A method of controlling bleeding in a mammal having a bleeding disorder associated with functional defects or deficiencies of at least one of FVIIa, factor VIII (FVIII) and factor IX (FIX), said method comprising administering the chemically-modified FVIIa molecule of any one of claim 1, 2 or 3.

8. A method of controlling bleeding in a mammal during surgery or trauma, said method comprising administering the chemically-modified FVIIa molecule of any one of claim 1, 2 or 3 in an amount effective to control bleeding.

9. A kit comprising an effective amount of the chemically-modified FVIIa molecule of any one of claim 1, 2 or 3 packaged in a container, said kit optionally containing a second therapeutic agent, and further comprising a label attached to or packaged with the container, the label describing the contents of the container and providing indications and/or instructions regarding use of the contents of the container for controlling bleeding in a mammal.

10. The kit of claim 9 wherein the container is a vial or bottle or prefilled syringe.

* * * * *

UNITED STATES PATENT AND TRADEMARK OFFICE
CERTIFICATE OF CORRECTION

PATENT NO. : 8,637,007 B2  
APPLICATION NO. : 11/956634  
DATED : January 28, 2014  
INVENTOR(S) : Peter Turecek et al.

Page 1 of 1

It is certified that error appears in the above-identified patent and that said Letters Patent is hereby corrected as shown below:

Title Page, Item (75), line 4, "Michel Canavaggio, Vienna (AT);" should be -- Michel Canavaggio, Vienna (AT), Deceased; --.

On the Title Page:

The first or sole Notice should read --

Subject to any disclaimer, the term of this patent is extended or adjusted under 35 U.S.C. 154(b) by 838 days.

In the Claims

At Column 18, line 44, "comprising," should be -- comprising: --.

Signed and Sealed this  
Twenty-first Day of April, 2015

Michelle K. Lee  
*Director of the United States Patent and Trademark Office*